United States Patent
Holland

[11] Patent Number: 5,957,904
[45] Date of Patent: Sep. 28, 1999

[54] EXTERNAL URINARY COLLECTION POUCH FOR FEMALES

[76] Inventor: Marlan J. Holland, 8775 San Gregorio, Atascadero, Calif. 93422

[21] Appl. No.: 08/941,981

[22] Filed: Oct. 1, 1997

Related U.S. Application Data

[63] Continuation-in-part of application No. 08/736,535, Oct. 24, 1996.

[51] Int. Cl.⁶ ..................................................... A61F 5/44
[52] U.S. Cl. ........................ 604/331; 604/349; 604/352; 604/329
[58] Field of Search ................................... 604/329–331, 604/349, 351, 352

[56] References Cited

U.S. PATENT DOCUMENTS

| | | | |
|---|---|---|---|
| 3,194,238 | 7/1965 | Breece | 128/295 |
| 3,995,329 | 12/1976 | Williams | 4/110 |
| 4,198,979 | 4/1980 | Cooney et al. | 128/295 |
| 4,246,901 | 1/1981 | Michaud . | |
| 4,350,785 | 9/1982 | Habib | 524/55 |
| 4,421,511 | 12/1983 | Steer et al. | 604/329 |
| 4,484,917 | 11/1984 | Blackmon | 604/327 |
| 4,496,355 | 1/1985 | Hall et al. | 604/327 |
| 4,568,339 | 2/1986 | Steer | 604/329 |
| 4,681,572 | 7/1987 | Tokarz et al. | 604/329 |
| 4,690,677 | 9/1987 | Erb | 604/329 |
| 4,795,449 | 1/1989 | Schneider et al. | 604/329 |
| 4,846,819 | 7/1989 | Welch | 604/329 |
| 4,889,532 | 12/1989 | Metz et al. | 604/330 |
| 4,889,533 | 12/1989 | Beecher | 604/330 |
| 4,904,248 | 2/1990 | Vaillancourt | 604/329 |
| 5,053,027 | 10/1991 | Manfredi | 604/327 |
| 5,263,947 | 11/1993 | Kay | 604/331 |
| 5,735,835 | 4/1998 | Holland | 604/331 |

OTHER PUBLICATIONS

Female Urinary Pouch 9840, "Instructions for using the Hollister® Female Urinary Incontinence Pouch," 1986.

Primary Examiner—Robert A. Clarke
Attorney, Agent, or Firm—Oppenheimer, Wolff & Donnelly LLP

[57] ABSTRACT

A female urinary collection device includes a receptacle pouch for collecting urine. The receptacle pouch includes a first area for securing adhesive strip to each buttock of a user to create a relatively rigid engagement of the device with the body. In the upper zone, there is a stretch loop and foam belt for securing the pouch around the waist. Inside the receptacle pouch, there is a reservoir of adsorbent material with a wick which exits the receptacle pouch through a tubing connected to an orifice in the receptacle. The receptacle pouch fits around the labia majora of the user. In some cases there are two outlets from the receptacle. The orifices are spaced from each other such that when a patient is lying on either one of her sides with the receptacle in place the one orifice would be relatively above the other thereby facilitating drainage of urine from the receptacle when the patient is lying on either one of her sides.

14 Claims, 4 Drawing Sheets

EXTERNAL URINARY COLLECTION POUCH FOR FEMALES

RELATED APPLICATION

This application is a continuation in part of application Ser. No. 08/736,535, filed Oct. 24 1996, the contents of which are incorporated by reference herein.

BACKGROUND

Urinary incontinence is a common medical problem. Providing an effective system for collecting urine from incontinent human females is valuable.

Many systems have been devised for attempting to collect urine from human females afflicted with incontinence. These systems include the use of catheters, incontinence pads, and diapers.

The use of invasive catheters through the urethra into the bladder is relatively uncomfortable and can be dangerous to health due to the high incidence of urinary tract infection. Absorbent products which hold urine in contact with the skin for extended periods of time contribute to skin breakdown, sometimes resulting in serious decubitus ulcers. On the other hand, the efforts to locate devices in and around the anatomy of the female tissues constituting the external organs of generation is difficult since it is particularly problematic to obtain a relatively leak proof fit. The anatomy of each user is different and hence it is difficult to find a universally acceptable external urinary collection device for neatly mating with the human body in an effective leak proof manner in which urine can be removed from the body after voiding.

The present invention is directed to minimizing the disadvantages of currently-known urinary collection devices for human females. The invention provides a collection device which is comfortable to wear, minimizes leakage of urine, and is adaptable to accommodate many shapes of different female anatomies.

SUMMARY

According to the invention, a female urinary collection device includes a generally pouch-shaped receptacle for collecting urine from the urethral orifice of a female user.

The receptacle includes a bottom edge portion and a side wall portion projecting upwardly therefrom. There is a lip portion having a portion of foam tape attached along the edge for providing a generally compliant area for engagement around the external labia majora of the user. The portion adjacent to the bottom edge includes two tapes which act as a primary securing means to secure the receptacle firmly to the buttocks of the user. Adhesive affects the fixation.

A second securing means located at the top of the side wall adjacent to an upper edge provides for the use of a stretch loop and foam material to extend around the waist and permit securing the receptacle in a relatively flexible manner with the body of the user. The top portion of the receptacle above the lip is relatively open to permit spreading around the body portion and to permit for an accommodating fit with the user.

Within the receptacle there is contained a cone-shaped reservoir which has a wicking system which drains through an orifice into a tubing. The tubing is located in the orifice between a base edge and a bottom edge of the receptacle.

The tubing is directed to a collection bag intended to be located below the receptacle. The wick feeds urine under gravity from the reservoir into the tube and down into the collection bag.

In another form of the invention there are provided two outlet orifices, the orifices being spaced from each other such that when a patient is lying on either side with the receptacle in place the one orifice would be relatively above the other.

In a further aspect of the invention there is tape provided to the receptacle for directly affixing the pouch to the perineum as well as the buttocks. Further, adhesive polyethylene foam side strips are affixed to the receptacle, the adhesive side strips being for attachment to the body in the crease between the thighs and the vulva.

The invention is further described with reference to the accompanying drawings.

DRAWINGS

DESCRIPTION

Figure 1:
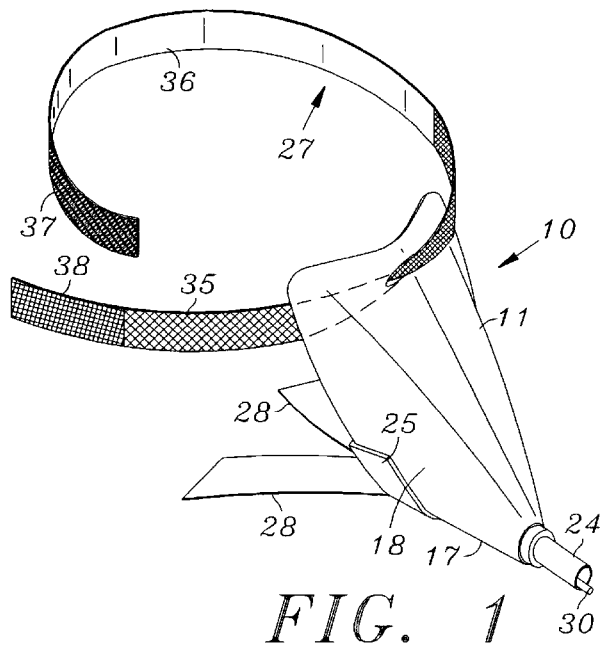
FIG. 1 is a perspective view of the device.

A female urinary collection device 10 comprises a generally pouch-shaped receptacle 11 for collecting urine from the urethral orifice of a female user 12.

The external organs of generation 13 in the human female are the mons Veneris, the labia majora 14, the menora, the clitoris, the meatus urinarius, and the orifice of the vagina. The meatus urinarius is also referred to as the orifice of the urethra. Below and rearwardly are the two buttock regions 15 of the human anatomy. Above the external organs and the buttock regions 15 is the waist portion 16 of the human form.

The receptacle pouch 11 has a bottom edge portion 17 and a side wall portion 18 projecting generally upwardly from the bottom edge portion 17. The side wall 18 and bottom edge 17 end in a lip portion 19 for sealing engagement with the area around the labia majora 14 of the user.

The side wall portion 18 is sized to extend from below the lips of the labia majora 14 to a position above those lips.

Figure 2:
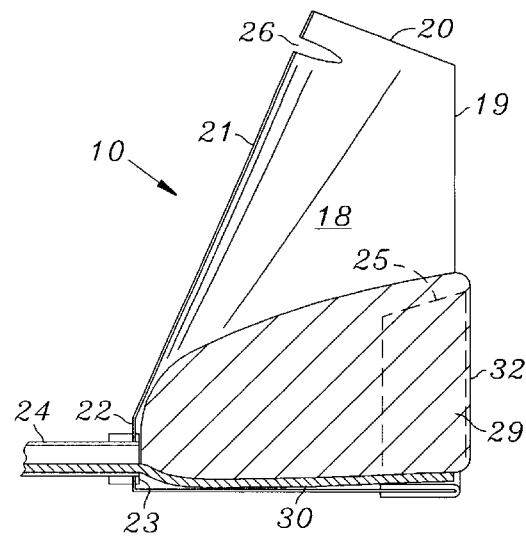
FIG. 2 is a side view of the device.
Figure 3:
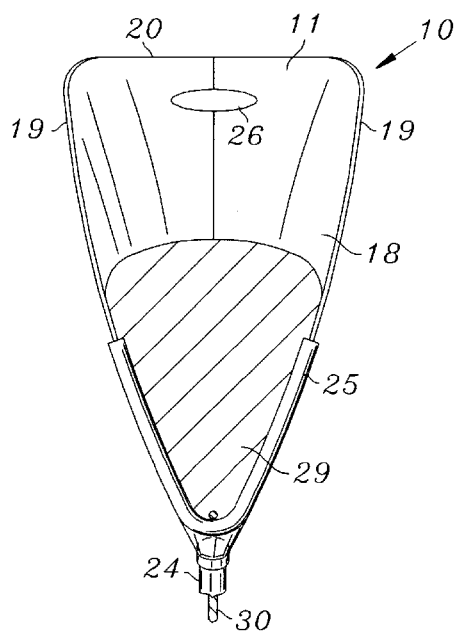
FIG. 3 is a front view of the device.
Figure 4:
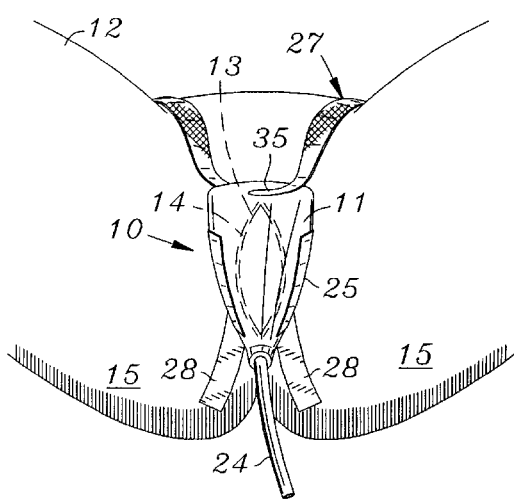
FIG. 4 is an end view of the device worn by a user.
Figure 5:
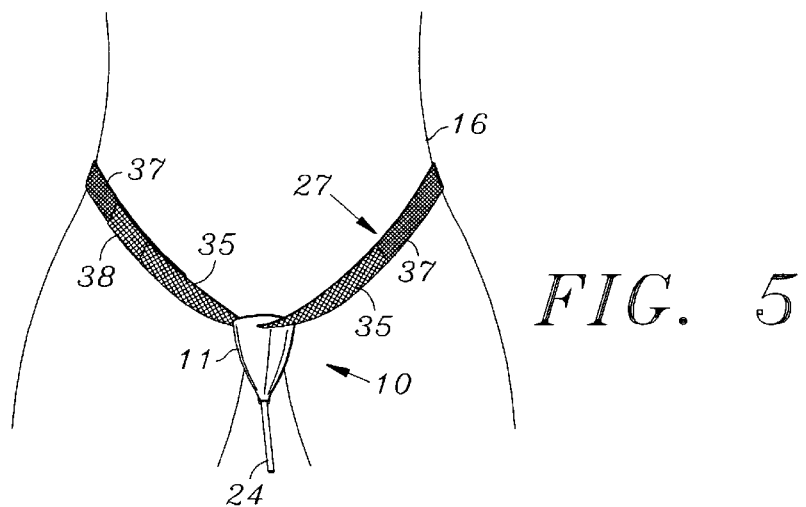
FIG. 5 is a top view of the device worn by a user.
Figure 6:
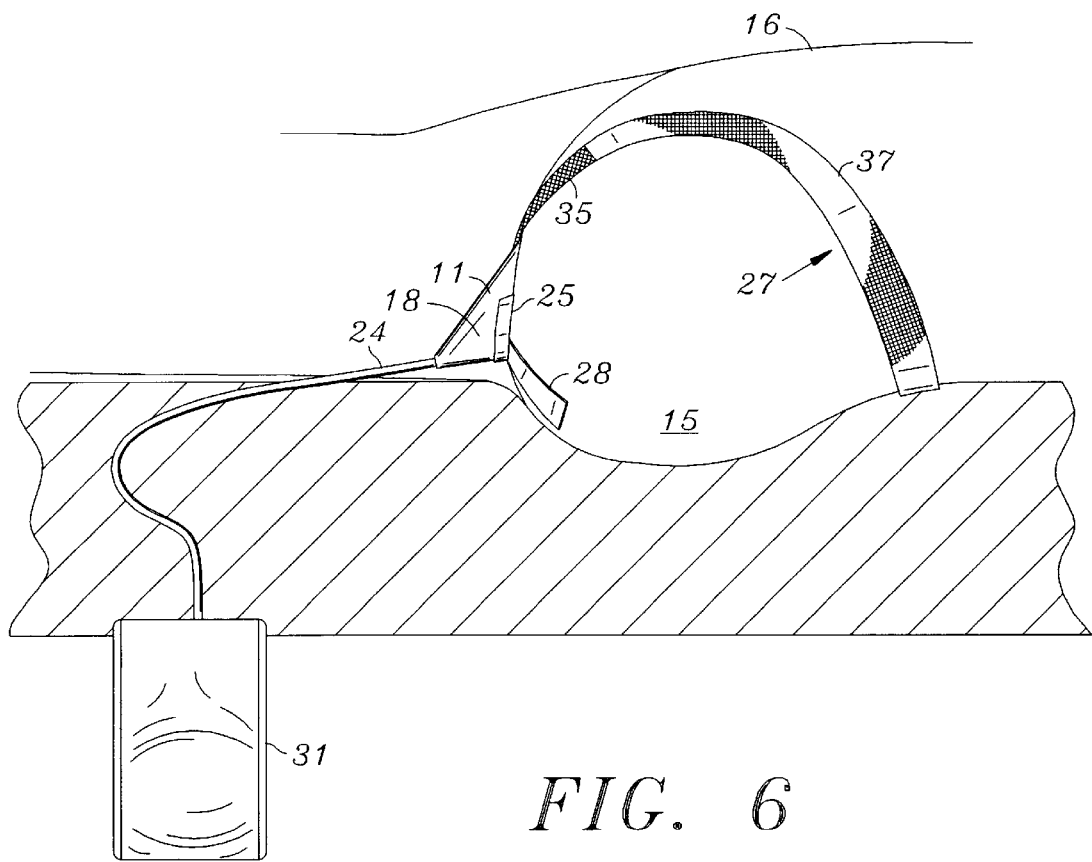
FIG. 6 is a side view of the device worn by a user lying horizontal on a mattress.

Generally, the receptacle pouch 11 as formed by the side wall, when viewed from the side (FIG. 2) and in collapsed or closed unused form, adopts a relatively trapezoidal profiled shape of two half mating side walls 18. There is the bottom edge 17, the lip portion 19, an upper edge portion 20, and a base edge portion 21. Between the intersection of the base edge and bottom edge portions, there is an edge section 22 for accommodating an orifice 22 through which a drain tube 24 passes. This intersecting edge 22 is a portion which is rectangularly formed relative to the bottom edge 17. In this sense, the generally trapezoidal sectional view has an additional small intersecting edge portion 22 thereby creating a pentagonal shape.

When viewed from the front in an opened operative position the two half side portions 18 form a contiguous sheet and is shaped to have a substantially horizontal upper edge 20. From the ends of the upper edge 20 there are two depending substantially vertical lip portions 19. About half way down their length these vertical sections start to converge ultimately to a point adjacent the bottom edge 17.

The shape of the receptacle pouch when viewed from the front, namely the direction normally adhering to the human form, can be considered to be a substantially curved edge triangulated form with rounded corners between the straight upper edge 20 and between the curved lips 19 and bottom edge 17. A generally curved V-shaped structure forms part of the wall of that triangulated shape.

The lip edge 19 includes a polyethylene closed cell foam tape 25 attached along the edge 19 to provide a soft surface to add comfort and reduce leakage of urine from the urethra and past the walls of the receptacle 11. The tape 25 is formed to cover the edge of the lip 19 both inside and outside of the receptacle pouch 11. As such, the tape 25 extends along the side wall 18 both on the inside of each side wall half portion 18 and the outside of each side wall half portion 18. The length of the tape 25 extends at least about two inches up the lip portion 19 of the receptacle pouch 11. When viewed from the front, the tape 25 forms a substantially V-shaped trough portion extending up one side wall half portion 18 through the bottom edge portion 17 and up the opposite side wall half portion 18.

Cut into the base edge 21 of the receptacle pouch 11, which is formed of a vinyl sheet, there is formed an oval slot 26 to accommodate a belt 27 of about 1.5 inches width. The upper edges of the vinyl sheet of each side wall half portion 18 can be separated so that it can spread apart and thus conform to different shapes of the human form. The belt 27 is preferably made of nylon stretch loop portion 35 and non-stretchable velfoam portion 36 which will extend up around the waist 16 and return to the receptacle 11. The belt also includes at an end of the stretch material, a portion of Velcro™ hook 38 for fastening means to loops 37 for effecting belt closure about the waist.

The major axis of the slot 26 is directed substantially parallel to the direction of the upper edge 20. By having the slot formed as an oval type shape, namely without sharp corners, there is less likelihood of tearing the pouch. Moreover, the major axis of the slot is smaller than the width of the belt, thereby minimizing belt slippage in the slot. The portion of the belt which is formed by the stretch material passes through the slot so that the slot is located at about the midpoint of the stretch material. The length of the stretch material could be about eight inches.

The belt 27 is substantially parallel to the slot when it passes through the slot, and it twists about 90° as it surrounds the waist 16 of the user. By having the belt 27 include a portion of stretch loop material 35, the receptacle 11 can move relative to the body portion as a user moves position, and the waist 16 of the user moves relative to other portions of the body. The belt portion includes the portion of non-stretchable material 36 to facilitate the fit about the waist.

Adjacent to the intersection of the bottom edge 17 which is located at the joinder of each side wall portion 18 and the lip 19, there is provided means for a first securing means.

This first securing means is in the form of two strips of tape 28 measuring about 1½ inches by 4 inches. One end of each of these strips of tape 28 is attached to a respective half portion of the side wall 11 of the receptacle pouch 11 on the outside of the receptacle pouch 11. The other end of the tape is for fixation by an adhesive to a respective buttock 15 of the user. In this manner, the tape 28 is provided with a first non-adhesive surface and a second adhesive surface on the opposite end. A suitable liner can be provided to cover the adhesive surface until the tape 28 is used. The tape has no appreciable stretch characteristic.

By having the tape 28 be fixed in this substantially rigid manner relative to the buttocks 15, the bottom edge 17 and lip portion 19 of the device 10 is substantially firmly located in adjacency with the lower or rear portion of the labia majora 14. In this manner, leakage is inhibited.

On the other hand, the relative flexibility with which the top edge portion 20 of the receptacle pouch 11 can move permits for adjustment of the receptacle pouch 11 relative to the body so that a conforming shape is maintained for the receptacle in position over the labia majora 14.

A cone-shaped reservoir 29 of highly adsorbent non-woven material is located in the receptacle pouch 11. In other forms the material can be an absorbent material. The reservoir material 29 includes a wicking system 30 which passes through an orifice 23 in the intersecting edge of the receptacle pouch.

The tubing 24 is a 0.400 inch outer diameter PVC tubing having an internal diameter of about 0.300 inch. It has a very soft durometer, and is about six inches or more in length. In some cases the tubing 24 can extend up to about 30 inches with the wicking element 30 inside. The wick 30 may extend for all or part of the length of the tubing 24. The tubing 24 is sealed with the perimeter of the orifice 23 in the receptacle pouch and the tubing 24 has a removable cap at the end. The end can also be connected to a collection drain bag or bottle 31 for collecting urine.

By having the wick 30 end at a position lower than the reservoir 29, a gravity effect is achieved and urine, from a void, drains from the reservoir 29 along the wick 30 into the collection drain or bag 31. The wick 30 can be located in the reservoir 29. The wick can be positioned at any convenient location within the reservoir. In another form of the device, the wick 30 is positioned substantially along the bottom edge 17 of the receptacle 11 so that a gravity effect of urine in the reservoir also works on the wick to cause urine to be absorbed by the wick 30 prior to draining into the collection bag 31. The wicking material is an absorbent or adsorbent material, but preferably an adsorbent material.

In considering the interaction of a fluid with a fibrous structure, there are two principal phenomena that need be considered: adsorption and absorption.

(1) The process of adsorption involves the collection of a fluid on the surface of a material. Some interactions can then occur, depending upon the nature of the material making up the surface, and the nature of the fluid or liquid involved. If the fluid can "wet" the surface material, it tends to spread out and wet as much of the surface as possible. If the liquid does not wet the surface, it tends to "bead up" and assume as small a surface volume as possible.

(2) The process of absorption, on the other hand, involves the penetration of the fluid into the interior of a material. This generally involves a molecular or similar attraction between the liquid and the solid material. As the solid imbibes the liquid, it tends to swell, which swelling continues until it is restricted by mechanical limits of the structure; at that point, the solid is saturated with the liquid and no further absorption takes place.

In the reservoir portion and wicking, it is preferred to form the reservoir from fibers that, of themselves, do not participate in absorption to any substantial degree. If absorbent or strongly hydrophilic fibers such as cotton or viscose rayon were employed, they would absorb the liquid involved and would swell to their maximum imbibed or swollen diameter. The swollen fibers would retain such liquid until it was removed, primarily by drying at an elevated temperature, or by gradual evaporation. There would be a modest amount of liquid contained in the void spaces between the swollen fibers, but the hydrophilic fiber surfaces would tend to attract the liquid, rather than transport it by a wicking process.

For optimum functionality, it is preferred to use hydrophobic fibers as the structural elements of the reservoir in the female urinary pouch. Such hydrophobic fibers do not imbibe the liquid and undergo swelling. Rather, with the proper rewetting character of the fiber surface, the fiber is partially wetted by the liquid. As the liquid encounters fibers that lie next to each other, it enters such capillary spaces and is moved by the attendant capillary pressure to spaces that have not yet been filled with liquid. Hence, the liquid is transported, or wicked, from regions containing liquid to regions that do not contain liquid.

By this process, the liquid can move within the structure until virtually all of the void space within the fibrous reservoir is filled. Further, as liquid is removed from one region of the fibrous reservoir, any excess liquid that is present moves into that void space through capillary pressure action. In essence, the liquid is transported from zones of high liquid content to zones of low liquid content by movement of the liquid along the surfaces of the fibers making up the reservoir.

For this action to progress effectively, the fibers employed in the reservoir structure and wicking are preferably hydrophobic, synthetic fibers. Further, such fibers must be prepared with a "finish" or surface lubricant that conveys a modest amount of wettability to the fiber, so that the wicking process can commence and continue. It is standard practice to provide fibers with a lubricating finish to facilitate the several mechanical operations that are normally applied in converting a fiber to a finished product. By addition of appropriate wetting agents to the lubricating materials, the finish can be formulated to give balanced wetting properties.

Suitable fibers for forming the liquid reservoir may include those produced from polyester, polyamide (nylon), polyolefin (such as polypropylene or polyethylene, or copolymers of propylene and ethylene) resins. The polyester fibers can be produced from homopolymer resin of polyethylene terephthalate, polybutylene terephthalate, polyethylene naphthenate, or similar polyester materials or copolymers. The nylon fibers can be produced from nylon-66 (polyhexamethylene adipate), nylon-6 (polycaprolactam) or similar polyamide or copolyamide materials. The polyolefin fibers can be produced from polypropylene, polyethylene or copolymers of propylene, ethylene, or similar olefin monomers or copolymers.

Other synthetic fibers possessing a hydrophobic nature can be used for this application; this may include, acrylic, modacrylic, cellulose acetate, vinyl fibers, spandex and other elastomeric fibers or blends of such fibers.

In order to form a reservoir and wicking that has suitable shape, integrity, and wet stability, it is necessary to incorporate binder fibers or particles in the reservoir and/or wicking. Such binder fibers or particles can be of the melting type, wherein the entire fiber or particle melts upon thermobonding of the reservoir structure and/or wicking.

A more preferred procedure is to use a bicomponent sheath/core type of binder fiber. Such a fiber has a core of higher melting point resin surrounded by a coating or sheath of lower melting point resin. For thermobonding, a temperature above the melting point of the sheath material is achieved, whereupon the sheath melts and forms a bond with any fiber touching the outer skin or sheath upon cooling. The advantage of this latter method is that the core of the binder fiber is not destroyed, but retains its fiber properties of strength and integrity throughout the thermobonding process, in contrast to the former method.

Other methods of bonding the fibrous reservoir structure can be used, but often with the introduction of some disadvantages. Such bonding may involve chemical latex binders or adhesives. Mechanical bonding, such as needlepunching or high pressure waterjet entanglement can be used.

When viewed from the side in the closed position, the leading edge 32 of the reservoir 29, namely the edge 32 adjacent to the lip 19, extends past the perimeter of the lip 19. This is to a position beyond the lip 19 so that it has an abutting relationship with the lower part of the labia majora 33. This facilitates the drainage of urine from the urethra into the reservoir 29.

When located in position, a compression effect takes place on the reservoir 29 thereby pushing the reservoir 29 substantially back into the perimeter as defined by the lip 19. This is achieved when the tapes 28 are pulled tight into position on the respective buttocks 15.

The receptacle 11 has a substantially funnel-type shape forming an apex towards the drain position where the orifice 23 is located. The reservoir 29 also has a largest area adjacent to the lip 19 and a decreasing area towards the aperture location. The reservoir 29 occupies about one-half of the volume of the receptacle pouch 11.

An aspect of the invention when related to the receptacle contacting the outside of the labia majora 14 is that there is believed to be no need for a sterile collection drain, bag or bottle 31 and supporting tubing 24. This provides an important advantage since multiple different units of this invention can be used in turn with a single collection drain bag or bottle system repetitively.

Many other forms of the invention exist each differing from others in matters of detail only.

In some situations there can be a collection device which is attached with the female anatomy within the area of the lips of the labia majora 14.

In other embodiments, for instance, instead of having an oval-shaped aperture 26 in the side wall 18 located transversely and substantially parallel to the upper edge for accommodating the stretch flexible loop, the means for fixing that loop to the receptacle pouch can be different.

Essentially, the combination of a flexible anchorage towards the top portion or edge 20 of the wall 18 of the receptacle pouch 11, and a relatively rigid engagement of the wall towards the bottom portion 17 of the receptacle pouch 11 is a desirable characteristic for effectively engaging the receptacle in a substantially leak proof manner relative to the body.

In other situations, the strips of tape 28 may adhere to the receptacle pouch 11 in different positions on the receptacle pouch.

In other situations, the reservoir 29 may occupy a different volume of the receptacle pouch 11. In further forms, the foam tape 27 may extend to a greater portion of the length of the lip namely to a position in closer adjacency to the upper edge.

Further, although the invention has been described generally in relation to a pouch, there are applications beyond a pouch type receptacle. For instance, the securing means may operate with different types of receptacles or other devices for securing to the body. The receptacles or devices can be formed of a rigid material.

Instead of a polyethylene closed-cell foam tape along the lip portion of the receptacle, other materials could be used. Materials other than vinyl could be used for the pouch.

There are aspects of the invention which are concerned with the receptacle, the reservoir and wicking material, and which are unrelated to the nature of the securing means with the body.

The modified device is now described.

Figure 7:
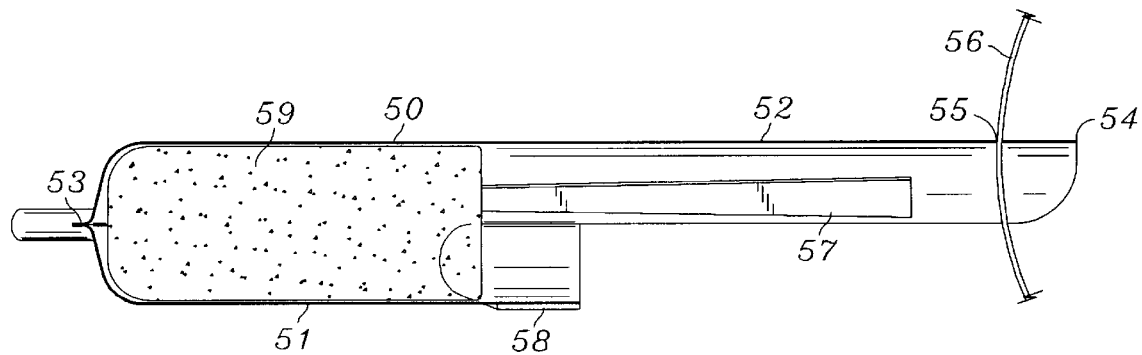
FIG. 7 is a sectional side view of a modified device.
Figure 8:
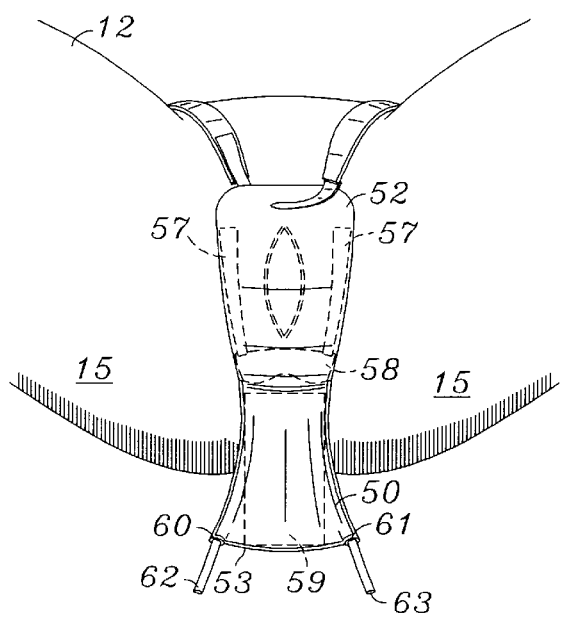
FIG. 8 is an end view of the modified device worn by a user.
Figure 9:
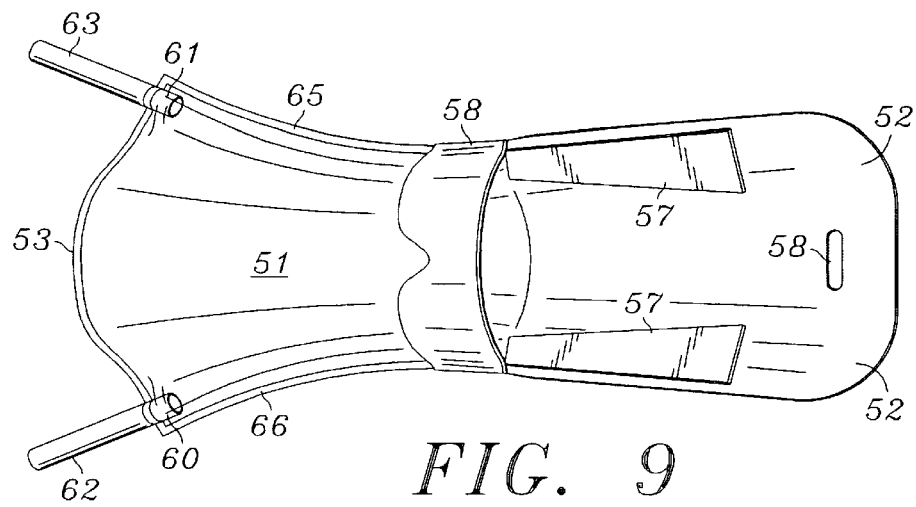
FIG. 9 is an underneath view of the device showing the receptacle and the tongue.

FIG. 7 shows a side view of a different embodiment of the collection device. The collection device has two mating sections 50 and 51, which are oppositely located relative to each other. Section 50 has an extended tongue portion 52. At the bottom end are the sections 50 and 51, which are welded together along location 53. The tongue end 52 extends from the portion 50 and towards the top portion 54 there is a slot 55 cut out for receiving a flexible band 56. Also extending above the tongue section are two elongated side strips 57. At the bottom top portion of the element 51, there is an adhesive strip portion 58. Within the receptacle formed by the portions 50 and 51, there is located an adsorbent material 59. Also located at the bottom portion 53 are two spaced outlet orifices 60 and 61. From each of these orifices 60 and 61, respectively, is an output showing 62 and 63.

With the arrangement as illustrated, the adhesive portion 58 would adhere to the buttocks portion of the person. The adhesive strip 57 running alongside the tongue 52, permits attachment of the collection device to the body in the crease between the thighs and the vulva of the patient.

Figure 10:
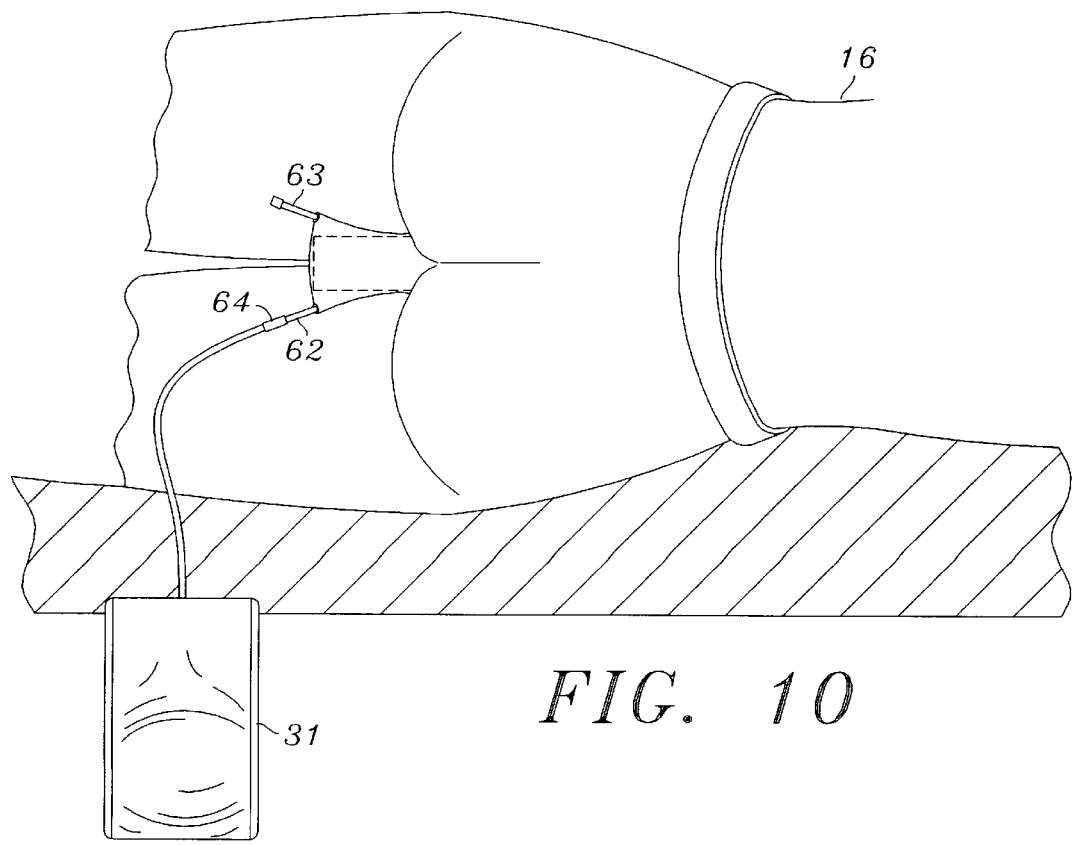
FIG. 10 is a side view of the device worn by a user lying on her side horizontally on a mattress.

By having the two orifices 60 and 61 on either side of the bottom portion 53, the device is particularly effective for use on patients when they lie on their side. This is often the case for patients who are prone to bed sores. As illustrated in FIG. 10, there is a situation where the tube 63 is connected to a drainage bag 31. When the patient is located in the opposite side position, the drainage tube 62 would be connected with the drainage bag 31.

In different situations, a Y connector between tube 62 and 63 can be provided so that there does not have to be a collection through a connector element 64 to connect the drainage bag 31 with the outlet tube 62 or 63.

As illustrated in the embodiment of FIGS. 7–10, the device is simple and less expensive to manufacture. The elements 51 and 52 are welded together along the end 53 and also the sides 65 and 66. This effectively creates a suitable bond to form the receptacle. The tongue 52 is an extension from the one element 50 as indicated.

The device of this invention is particular advantageous. The two outlets produce more effectiveness with side-lying patients. The particular shape of the receptacle is one which has a relatively increased volume capacity. The adhesive attaches to the perineum as well as to the buttocks and this also provides for better security with the body. The adhesive polyethylene foam side strips 57 are added to reduce leakage. In different arrangements, there may or may not be a wick in this embodiment. As illustrated in the particular figures, there is no wick.

The invention is to be determined solely by the following claims.

I claim:

1. A female urinary collection device comprising:
  a receptacle for collecting urine from the urethral orifice of a female user, the receptacle having an edge portion and a side wall portion projecting generally from the edge and a lip portion for sealing engagement with the human tissue substantially outside the area of the labia majora of the user, two outlet orifices, the orifices being spaced from each other such that when a patient is lying on either one of her sides with receptacle in place the one orifice would be relatively above the other thereby facilitating drainage of urine from the receptacle when the patient is lying on either one of her sides.

2. The device as claimed in claim 1 including a first securing device for the receptacle on the body, the first securing device including adhesive tape for connection with each respective buttock, thereby to locate the edge portion of the receptacle relatively securely in relation to the buttocks.

3. The device as claimed in claim 2 including a second securing means for the receptacle the second securing means including a flexible strap, the flexible strap being for location about the waist of a user thereby to permit a degree of relative movement between the receptacle and the user in the region of the location of the second securing means.

4. The device as claimed in claim 3 including means for securing the second securing means to the side wall portion, such securing means including a slot cut in a wall portion for accommodating a belt of nylon stretch loop and foam material, the belt being for extending around the waist of a user.

5. The device as claimed in claim 1 including a securing means for the receptacle, the securing means including a flexible strap, the flexible strap being for location about the waist of a user to thereby permit a degree of relative movement between the receptacle and the user in the region of the location of the securing means.

6. The device as claimed in claim 1 including a polyethylene foam adhesive strips located along at least a portion of a tongue portion extending from the receptacle, the adhesive side strips being for attachment to the body in the crease between the thighs and the vulva.

7. The device as claimed in claim 1 wherein the receptacle is formed of a vinyl material, and wherein the receptacle includes two mating walls, one of the walls having a tongue portion, the tongue portion being for receiving the second securing means.

8. The device as claimed in claim 1 including a reservoir of adsorbent material for location in the receptacle.

9. The device as claimed in claim 1 including a tubing for connection to a respective one of the outlet orifices for permitting removal of urine from the receptacle.

10. A female urinary collection device comprising a receptacle for collecting urine from the urethral orifice of a female user, the receptacle having a bottom edge portion and a side wall portion projecting generally from the bottom edge and in a lip portion for sealing engagement with the human tissue of the user, the side wall portion including at least two zones for anchoring securing means to the side wall, a first securing means being located at a position with the side wall and for permitting the securing means to engage each of two buttocks of a user, and a second securing means being located at a position whereby the second securing means is for securing the receptacle to a portion of the body above the external organs of generation, and adhesive strips located along at least a portion of a tongue portion extending from the receptacle, the adhesive side strips being for attachment to the body in the crease between the thighs and the vulva.

11. A female urinary collection device comprising a receptacle for collecting urine from the urethral orifice of a female user, the receptacle having a bottom edge portion and a side wall portion projecting generally from the bottom edge and in a lip portion for sealing engagement with the human tissue of the user, the side wall portion including at least two zones for anchoring securing means to the side wall, a first securing means being located at a position with the side wall and for permitting the securing means to engage each of two buttocks of a user, and a second securing means being located at a position whereby the second securing means is for securing the receptacle to a portion of the body above the external organs of generation, and the first securing device including adhesive tape for connection with each respective buttock, thereby to locate the bottom edge portion of the receptacle relatively securely in relation to the buttocks and the second securing means including a flexible strap, the flexible strap being for location about the waist of a user thereby to permit a degree of relative movement between the receptacle and the user in the region of the location of the second securing means, and a tongue portion extending from the receptacle, the tongue having an adhesive for attachment to the body.

12. The device as claimed in claim 11 including a reservoir of adsorbent material for location in the receptacle.

13. A female urinary collection device comprising a receptacle for collecting urine from the urethral orifice of a female user, the receptacle having a first member and a second mating member, the second mating member being of a similar shape to the first member and in addition having a tongue extending from a top end portion, there being a bottom edge portion and two side edge portions which are in substantially mating relation between the first and second members, a lip portion on the first member for sealing and anchored engagement with the human tissue of the user, the receptacle including two spaced apart outlet orifices, the outlet orifices being located substantially at two opposed corners removed from the tongue portion and the lip portion, a tubing for connection to each outlet orifice for permitting removal of urine from the receptacle.

14. The device as claimed in claim 13 including a reservoir of material for location in the receptacle, and wherein the reservoir is an adsorbent material.

* * * * *